United States Patent
Reinhold et al.

(10) Patent No.: US 11,105,783 B2
(45) Date of Patent: Aug. 31, 2021

(54) ARRANGEMENT AND METHOD FOR CALIBRATING AT LEAST TWO SENSORS IN PARALLEL

(71) Applicant: Endress + Hauser Conducta Gesellschaft für Mess- und Regeltechnik mbH + Co. KG, Gerlingen (DE)

(72) Inventors: Andrea Reinhold, Chemnitz (DE); Stefanie Horn, Waldheim (DE)

(73) Assignee: Endress + Hauser Conduct GmbH + Co. KG, Gerlingen (DE)

( * ) Notice: Subject to any disclaimer, the term of this patent is extended or adjusted under 35 U.S.C. 154(b) by 811 days.

(21) Appl. No.: 13/934,517

(22) Filed: Jul. 3, 2013

(65) Prior Publication Data

US 2014/0012530 A1 Jan. 9, 2014

(30) Foreign Application Priority Data

Jul. 9, 2012 (DE) .......................... 202012102521.3

(51) Int. Cl.
*G01N 33/00* (2006.01)
*G01N 27/416* (2006.01)

(52) U.S. Cl.
CPC ......... *G01N 33/00* (2013.01); *G01N 27/4165* (2013.01)

(58) Field of Classification Search
CPC .................................................. G01N 27/4165
See application file for complete search history.

(56) References Cited

U.S. PATENT DOCUMENTS

| | | | | |
|---|---|---|---|---|
| 4,912,417 A | * | 3/1990 | Gibboney | G01N 27/4165 204/400 |
| 6,365,424 B1 | * | 4/2002 | Bauer | G01D 11/245 257/690 |
| 7,924,017 B2 | † | 4/2011 | Ammann | |
| 2007/0257791 A1 | * | 11/2007 | Arita | G08B 25/10 340/539.1 |
| 2009/0030293 A1 | * | 1/2009 | Cooper | A61B 1/00016 600/302 |
| 2009/0112191 A1 | * | 4/2009 | Boyden | A61M 31/002 604/891.1 |
| 2010/0211832 A1 | * | 8/2010 | Buschnakowski | G05B 19/4185 714/57 |

(Continued)

OTHER PUBLICATIONS

Reference No. 1 is a "User Manual" for the "cellferm-pro," from DASGIP mbH, dated Jan. 2000, pp. 1-95, DASGIP mbH Germany.†

(Continued)

*Primary Examiner* — Kyle R Quigley
(74) *Attorney, Agent, or Firm* — Christopher R. Powers; Endress + Hauser (USA) Holding Inc.

(57) ABSTRACT

A arrangement for calibrating at least two sensors in parallel, including a data processing unit, especially a measurement transmitter for a multisensor system or a computer, wherein the data processing unit has an interface, via which the at least two sensors are connected via separate transmission lines for transmission of data, and wherein the data processing unit is embodied to perform calibrations of the at least two sensors in parallel and independently of one another.

10 Claims, 1 Drawing Sheet

(56) References Cited

U.S. PATENT DOCUMENTS

2012/0330596 A1* 12/2012 Kouznetsov ....... G01N 33/0006
702/104

OTHER PUBLICATIONS

Reference 2 provides the "Operating Instructions" for the "DCU System for BIOSTAT Qplus Digital Measurement and Control System," dated Oct. 2008, pp. 1-94.†
Reference No. 3 is a sales brochure for the BIOSTAT Qplus, dated 2009, pp. 1-8, Germany.†
Reference No. 4 is an "Operator's Manual" for the "Multi-Parameter TROLL 9500," dated Jan. 2009, pp. 1-164.†
Reference No. 6 is a manual dated Apr. 2010 providing the general introductory information for the iSense ISM Asset Suite, Mettler-Toledo AG, pp. 1-42, Switzerland.†
Reference No. 7 is an "Advertorial" titled "Combining Small Scale Systems and Bioreactors with Parallel Cultivation and Software Intelligence" for DASGIP Technology bioreactor systems, dated 2005, pp. 1-2, Industry Yearbook.†
Reference No. 1 is a "User Manual" for the "cellferm-pro" from DASGIP mbH dated Jan. 2000, including pp. 1-95, DASGIP mbH Germany.†
Reference No. 2 is the "Operating Instructions" for the "DCU System for BIOSTAT Qplus Digital Measurement and Control System" dated Oct. 2008, including pp. 1-94.†
Reference No. 3 is a sales brochure for the BIOSTAT Qplus, dated 2009, including pp. 1-8, Germany.†
Reference No. 4 is an "Operator's Manual" for the "Multi-Parameter TROLL 9500" dated Jan. 2009, including pp. 1-164.†
Reference No. 6 is a manual dated 2010 providing the general introductory information for the iSense ISM Asset Suite, Mettler-Toledo AG, including pp. 1-42, Switzerland.†
Reference No. 7 is an "Advertorial" for DASGIP Technology bioreactor systems, dated 2005, including pp. 1-2, Industry Yearbook.†

* cited by examiner
† cited by third party

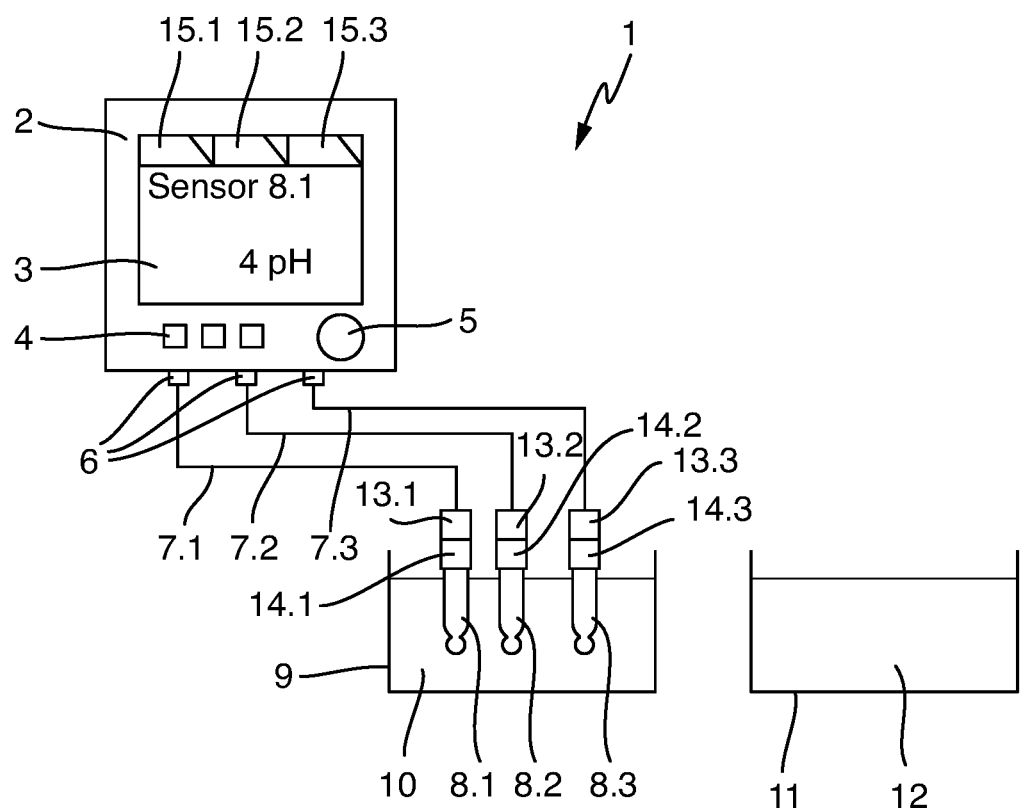

ARRANGEMENT AND METHOD FOR CALIBRATING AT LEAST TWO SENSORS IN PARALLEL

TECHNICAL FIELD

The invention relates to an arrangement and method for calibrating at least two sensors in parallel.

BACKGROUND DISCUSSION

Sensors are applied for many uses in automation technology, especially in process automation technology. Especially, those that serve for measuring process variables. Based on currently registered, measured values of the process variables, for example, control procedures can be directed. Sensors often applied and well known and established in process measurements technology include, for example, fill level sensors, flow sensors, pressure- and temperature sensors, pH-sensors, pH-redox sensors, conductivity sensors, turbidity sensors, oxygen sensors and other sensors for registering concentration of dissolved gases or other substances, especially in liquid media.

These sensors register the respectively to be determined, measured variable and transduce it into an electrical signal. In many measuring arrangements with such sensors, their signals are registered by a measurement transmitter, further processed and then, in further processed form, either output via a display unit, e.g. a display, of the measurement transmitter, so the user can read the information, or output via an interface of the measurement transmitter to another unit superordinated to the measurement transmitter. The superordinated unit can be a superordinated control system, or a control unit, such as, for example, a programmable logic controller. Such a superordinated unit can serve for, among other things, process control (open or closed loop) based on the measured values registered by means of the sensors. In some applications, one or more sensors can also be connected to a computer, e.g. a PC, laptop, tablet-PC or a smart phone serving as a superordinated unit. In this case, a part of the measurement transmitter functionality, namely the registering and, in given cases, amplification of an analog, primary signal and conversion into a digital measurement signal, which can be output to a superordinated unit, can be implemented in an on-site electronics integrated in the sensor. The computer can contain an operating program, which can further process and/or display the digital measurement signals forwarded from the sensor to the computer.

A measurement transmitter serves especially for converting a measurement signal, e.g. a voltage, delivered from the sensor, and representing the measured value registered by the sensor, into a measured value in the physical units of the process parameter to be measured by the sensor. This occurs in modern measurement transmitters, most often, in that the analog signal generated by the sensor is, first of all, converted into a digital signal, and the digital signal is then sent to a processor of the measurement transmitter, where an operating program converts the digital signal by means of a predetermined calculational recipe into a corresponding measured value. If the sensor is, for example, a potentiometric pH-sensor, it produces, first of all, an analog voltage signal, which is registered between a measuring- and a reference electrode of the sensor. This signal is converted by means of an analog/digital converter into a digital signal, which is converted by a processor of the associated measurement transmitter into a pH-value based on a predetermined calibration function, frequently a calibration line defined by a zero-point and a slope. Additionally, the measurement transmitter can perform temperature compensation, since the voltage signal delivered by the pH-sensor is influenced also by temperature. For this, the processor executes a corresponding operating- or measuring program, which is stored in a program memory of the measurement transmitter for execution by the processor.

The sensors to be used in the process must be calibrated, at least before start-up. Some of the above mentioned sensors, especially pH- or pH-redox sensors, and also oxygen- and turbidity sensors, are frequently even recalibrated in regular intervals.

In such case, the deviation of the measured value delivered by the sensor from a standard is ascertained. Following the calibration, an adjustment of the instrument can be performed. This means, for instance, adapting the calculational recipe, according to which the sensor or the measurement transmitter determines a measured value from a measurement signal, in such a manner that the measurement signal produced in the calibrating by the sensor is converted into the correct measured value. For example, the calibration line, respectively its zero-point and/or its slope, can be correspondingly adapted. Frequently, the adjustment is likewise referred to as calibrating. Here and in the following, the adjusting is considered to be an optional component of a calibration.

For calibrating a pH-sensor, such is immersed into one or more solutions of known pH-value, the measured value produced, in each case, by the sensor is registered and the registered measured value is compared with the expected, known pH-value of the respective solution. Frequently used for this are buffer solutions. In a following adjusting step, the calibration line, respectively the associated values of zero-point and slope of the pH-sensor, can be so adapted that, from the measurement signal delivered by the sensor in the one or more buffer solutions of known pH-value, the correct measured value is calculated. Zero-point and slope of the calibration line are also referred to as calibration parameters. If the sensor is used in measurement operation, the calibration line defined by the last ascertained calibration parameters is used for deriving the measured values from the measurement signals of the sensor.

Some of the initially mentioned sensors, especially pH- or pH-redox sensors, oxygen- and turbidity sensors, which are frequently subjected also to a regular re-calibration, are, as a rule, embodied as measuring probes situated remotely from the measurement transmitter and connected with it via cable connections or wirelessly via radio. This separation permits the sensors to be regularly separated from the measurement transmitter, for recalibration or replacement.

In German patent application DE 10 2009 029 495 A1, for example, a measurement transmitter for a multisensor system is described, which has a processor for processing in- and output signals. The processor is connected with an interface, to which one or more sensors is/are connected for transmission of data via a transmission line, wherein in the case of communication between the process sensor and the interface (respectively each of the sensors connected with the interface), different data transmission rates can occur. Connectable to this measurement transmitter are, consequently, a plurality of sensors, even such, which work according to different principles of operation. For this, the interface includes for each sensor a function module associated with this sensor. A function module associated with a sensor is, in each case, connected via a separate transmission line with the respective sensor.

The sensors are, as a rule, calibrated by the manufacturer or—when a regular recalibration during the lifetime of the sensors is desired—also by the user. For this, the sensors with the measurement transmitter are connected to an arrangement for calibrating the sensors and, such as above described, calibration then proceeds.

Known measurement transmitters known until now permit, however, only the calibrating of one sensor at a time, even when a number of sensors are connectable to the measurement transmitter. Especially, calibrations performed at the sensor manufacturer consume much time, since all sensors to be delivered by the manufacturer must be calibrated individually, one after the other.

SUMMARY OF THE INVENTION

An object of the invention, therefore, is to provide an arrangement for calibrating a plurality of sensors that enables reducing the time consumed for calibrating a plurality of sensors.

This object is achieved by an arrangement for calibrating at least two sensors in parallel,
comprising a data processing unit, especially a measurement transmitter for a multisensor system or a computer, wherein the data processing unit has an interface, via which the at least two sensors are connected via separate transmission lines for transmission of data, and
wherein the data processing unit is embodied to perform calibrations of the at least two sensors in parallel and independently of one another.

Therewith, it becomes possible to calibrate at least two, preferably four sensors, independently of one another and in parallel, i.e. at the same time. This permits reducing the time associated with calibrating a plurality of sensors to a fraction of the time used in the previous procedure.

The data processing unit can be, for example, a measurement transmitter or a conventional computer, e.g. a PC, a laptop, a smart phone or a tablet PC.

The data processing unit, especially the measurement transmitter, can have a processor, which is connected with the interface for processing in- and output signals,
wherein the data processing unit, especially the measurement transmitter, contains an operating program for the at least two sensors and the operating program is executable by the processor.

For parallel measuring and/or calibrating, each of the sensors connected with the data processing unit, especially the measurement transmitter, can have its own measurement channel, wherein the operating program is embodied to operate the measurement channels in parallel and independently of one another.

For performing a parallel calibrating of a plurality of sensors, the operating program can especially be embodied to store and display calibration measured values registered by the sensors at the same time. For this, the operating program can, for example, provide a selection menu, with which the user can alternate between a measuring mode of the operating program and a calibration mode. To this end, the data processing unit, especially the measurement transmitter, can have corresponding input elements, e.g. switches or a touch display. In the calibration mode, the current measured values of the sensors can be displayed in a shared window.

The operating program can, in another embodiment, be instantiable multiple times, wherein each instance of the operating program is associated uniquely with one of the sensors connected to the data processing unit, especially the measurement transmitter, and is executable by the processor in parallel with, and independently of, other instances, in order to operate the sensors in parallel and independently of one another, especially to calibrate the sensors independently of one another.

For example, each instance of the operating program can have its own window on a display of the data processing unit, especially the measurement transmitter. A service person, who is performing the calibrating with the arrangement, can switch back and forth between the individual windows associated with the sensors to be calibrated or display all window simultaneously, in order to monitor the progress of the calibration of each of the sensors. For this, the data processing unit, especially the measurement transmitter, can have corresponding input elements, e.g. switches or a touch display.

The at least two sensors can be embodied for measuring one and the same parameter, especially the pH-value. For calibrating, the sensors to be calibrated in parallel can be simultaneously in contact with a calibration medium. If the sensors to be calibrated in parallel are pH-sensors, these can be simultaneously immersed in a container containing a buffer solution.

It is equally an option that at least two sensors of the arrangement are embodied for measuring different parameters, i.e. that sensors for measuring different parameters, e.g. one or more pH-sensors together with one or more oxygen sensors, are calibrated in parallel.

The sensors can include, accommodated in the sensor housing, for example, in a plug head, an on-site electronics, which has a memory, which the data processing unit, especially the measurement transmitter, can access for executing the operating program. The memory can serve to store the calibration parameters, e.g. zero-point and slope, of a calibration function, ascertained in a calibration, in the memory of the sensors for adjusting the sensors, so that the sensor carries its own calibration parameters, for example, calibration parameters ascertained by the manufacturer, even when it is connected later to another data processing unit, especially another measurement transmitter, for monitoring a process of a user.

The on-site electronics can be embodied to convert an analog, primary, measurement signal of the sensor into a digital measurement signal. In given cases, the measurement signal can be amplified before or after the analog to digital conversion. In this embodiment, the sensor outputs digital measurement signals to the data processing unit, especially the measurement transmitter.

The operating program of the data processing unit, especially the measurement transmitter, can be correspondingly embodied to store currently ascertained calibration data, for example, the calibration parameters, zero-point and slope, in the memory of the sensor.

The invention includes also a method for the parallel calibrating of at least two sensors, especially by means of the above described arrangement. The method includes:
connecting the at least two sensors via separate transmission lines for transmission of data to an interface of a data processing unit, especially a measurement transmitter or a computer, for a multisensor system; and
calibrating the at least two sensors in parallel and independently of one another by means of the data processing unit, especially the measurement transmitter or computer.

For the case, in which the at least two sensors are embodied for measuring one and the same parameter, for example, the pH-value, an oxygen concentration, a solids content or a conductivity, the at least two sensors can be simultaneously placed in contact with a calibration medium. For example, they can be simultaneously immersed in a calibration liquid contained in a container. The measured values registered, in such case, by the sensors and output to the data processing unit can be used by the data processing unit for calibration. If the sensors are pH-sensors, a buffer solution of known pH-value can serve as calibration medium.

The data processing unit can, such as already above described, contain an operating program executable by the data processing unit. For performing a calibrating, especially as initiated by a selection made by an user by means of one or more input elements of the data processing unit, the operating program can be operated in a calibration mode. In the calibration mode, the calibration measured values registered by the sensors during the calibrating can be recorded by the operating program and displayed on a display system of the data processing unit, especially in a shared presentation, e.g. in a shared window or in a plurality of windows shown simultaneously by the display system.

The calibrating, which can, as above mentioned, optionally include an adjusting, can be followed by the user by means of the display system of the data processing unit.

BRIEF DESCRIPTION OF THE DRAWINGS

The invention will now be described in greater detail based on the sole FIGURE, FIG. 1, of the drawing.

FIG. 1 shows an arrangement for parallel calibration of a plurality of pH-sensors.

DETAILED DISCUSSION IN CONJUNCTION WITH THE DRAWING

The measuring arrangement 1 shown schematically in FIG. 1 includes a measurement transmitter 2 having a display element, e.g. a display, 3, as well as interaction elements, e.g. keys, 4 and/or a rotate-push switch 5, which serve to input commands into the measurement transmitter 2 or to confirm reports of the measurement transmitter 2. Measurement transmitter 2 includes in the example shown here an interface with three connections 6, to which three pH-sensors 8.1, 8.2, 8.3 are connected by means of separate transmission lines 7.1, 7.2, 7.3.

Via the transmission lines 7.1, 7.2, 7.3 connected with the interface, the pH-sensors 8.1, 8.2, 8.3 can be supplied with energy by the measurement transmitter 2 and exchange data with the measurement transmitter 2. The interface includes for this, for each of the sensors 8.1, 8.2, 8.3 to be connected, a function module (not shown) associated with the sensor and connected with the respective transfer line 7.1, 7.2, 7.3 of the sensor. Measurement transmitter 2 includes for its part a processor (not shown) accommodated in the measurement transmitter housing and connected with the interface. In this way, there is formed for each sensor 8.1, 8.2, 8.3, via the function module associated with it, a separate data transfer channel to the processor. Thus, the sensors 8.1, 8.2, 8.3 can, simultaneously and independently of one another, exchange data with the processor via the function modules respectively associated with them. Data overlapping is, in such case, excluded as a source of error. Details for the construction of the measurement transmitter and the interface are presented, for example, in DE 10 2009 029 495 A1.

The processor is correspondingly embodied to receive input signals from, and to output output signals to, the sensors 8.1, 8.2, 8.3. The processor is furthermore embodied to execute an operating program associated with it, for example, an operating program stored in a program memory of the measurement transmitter 2, in order to convert measurement signals output from the pH-sensors into a pH-value and to output such via the display 3.

The sensors 8.1, 8.2, 8.3 have, in each case, liquid tightly sealed relative to the environment, a plug head 14.1, 14.2, 14.3, in which an on-site electronics (not shown) is accommodated. The on-site electronics includes, on the one hand, circuit means for registering analog voltage signals output by the pH-sensors and representing the pH-measured value currently registered by the respective sensors. Furthermore, the on-site electronics includes an analog/digital converter, which generates from the analog voltage signal a digital signal, which is, in given cases, further processed by means of the on-site electronics or directly output via the transmission lines 7.1, 7.2, 7.3 to the measurement transmitter 2. The on-site electronics includes in the here described example, moreover, a data memory, in which calibration data of the sensors 8.1, 8.2, 8.3 are stored. The sensor plug heads 14.1, 14.2, 14.3 are releasably connected with the transmission lines 7.1, 7.2, 7.3 via socket elements 13.1, 13.2, 13.3. The measurement transmitter 2 can access data stored in the data memory via the transmission lines 7.1, 7.2, 7.3.

For performing a parallel calibrating of the sensors 8.1, 8.2, 8.3, these are immersed in a buffer solution 10 contained in a first container 9. Buffer solution 10 has a constant, known pH-value. The measurement signals of the sensors are transmitted in the described manner to the measuring transducer 2 and processed there. The operating program executable by the processor of the measurement transmitter 2 includes a calibration routine, by means of which it can calibrate a plurality of sensors 8.1, 8.2 and 8.3 simultaneously, in parallel and independently of one another. In order to invoke the calibration routine, a user can select a calibration mode of the operating program from a selection menu shown on the display. By means of the selection menu, the user can later return to a measuring mode. This ends the calibration routine.

The operating program is instantiable multiple times in such a manner that an instance of the program is associated with each sensor 8.1, 8.2, 8.3. In this way, the sensors 8.1, 8.2, 8.3 can be operated independently of one another, especially calibrated independently of one another. Associated with each instance is a window shown on the display 3 of the measurement transmitter. Sensor data and current measured values are shown in the windows. In the example shown here, the user can jump back and forth between the different windows associated with the sensors 8.1, 8.2, 8.3 via the tabs 15.1, 15.2 and 15.3. However, options are also to have the windows be visible all together at the same time or to have the calibration measured values, respectively other calibration reference data, appear for all sensors in one shared window.

The calibration routine of the operating program executable by the processor of the measurement transmitter 2 is embodied to detect the reaching of a stable measured value based on predetermined stability criteria and, as soon as a stable measured value is recognized, to store such intermediately. As soon as all sensors 8.1, 8.2 and 8.3 immersed in the first buffer solution 10 reach stable measured values and these are stored interiorly, the sensors can be removed from the first buffer solution 10, in given cases, rinsed with deionized water and then immersed in a second buffer solution 12, which is contained in a second container 11. The second buffer solution 12 has a pH-value different from the pH-value of the first buffer solution 10. Preferably, the pH-values of the two buffer solutions differ by at least two pH-levels. The calibration routine is furthermore embodied to detect also in the second buffer solution the reaching of a stable measured value of the sensors 8.1, 8.2 and 8.3 and to store likewise these values intermediately. For adjusting the sensors 8.1, 8.2 and 8.3, the calibration routine can, moreover, be embodied, for example, upon an input of a service person to the measurement transmitter 2, to adapt the calibration parameters of the sensors 8.1, 8.2 and 8.3 based on the two intermediately stored, measured values and to store the adapted calibration parameters as current calibration parameters in the memory of the measurement transmitter 2 and/or in the memory of the on-site electronics of the sensors 8.1, 8.2 and 8.3.

The so calibrated sensors 8.1, 8.2 and 8.3 are, thereafter, ready for use and can be connected at a predetermined measuring point to a measurement transmitter present there for performing measurements.

The invention claimed is:

1. An arrangement for calibrating at least two sensors in parallel, comprising:
    at least two sensors, each including a memory therein;
    a data processing unit embodied to perform calibrations of the at least two sensors in parallel and independently of one another via a calibration routine, the data processing unit including an interface, via which the at least two sensors are connected via separate transmission lines for transmission of data, and a processor, which is in communication with the interface for processing input and output signals, wherein each sensor connected with the data processing unit is associated with its own measurement channel; and
    an operating program for the at least two sensors, the operating program associated with said data processing unit and executable by the processor, wherein the operating program includes the calibration routine and is configured to store currently ascertained calibration data for each of the at least two sensors in each corresponding memory and to operate the measurement channels associated with the sensors in parallel and independently of one another,
    wherein the operating program is instantiable multiple times, and each instance of the operating program is associated uniquely with one of the sensors connected to said data processing unit and is executable by the processor in parallel with and independently of other instances such that the sensors are calibrated in parallel and independently of one another,
    wherein said data processing unit is a measurement transmitter for a multisensor system, the measurement transmitter configured to convert measurement signals from the at least two sensors into corresponding measured values using the calibration routine, to perform temperature compensation of the corresponding measured values, and to access each memory for executing the operating program, and
    wherein the calibration routine, executable by the processor of the measurement transmitter, includes determining for each sensor when a stable measured value of each corresponding measured value is attained based on predetermined stability criteria, whereupon each stable measured value is stored temporarily, adapting calibration parameters of the sensors based on the stable measured value stored temporarily by the calibration routine, and storing the adapted calibration parameters in the corresponding memories of the sensors.

2. The arrangement as claimed in claim 1, wherein:
    the operating program is embodied to display measured values registered by the sensors during the calibrating simultaneously by means of a display system of said data processing unit.

3. The arrangement as claimed in claim 1, wherein the at least two sensors are embodied for measuring one and the same parameter.

4. The arrangement as claimed in claim 1, wherein:
    at least two sensors of the arrangement are embodied for measuring different parameters.

5. The arrangement as claimed in claim 1, wherein all sensors of the arrangement are embodied for measuring a pH-value.

6. The arrangement as claimed in claim 1, wherein all sensors of the arrangement are pH-sensors.

7. A method for calibrating at least two sensors in parallel, comprising the steps of:
    connecting the at least two sensors via separate transmission lines for transmission of data to an interface of a data processing unit, said data processing unit including a measurement transmitter or a computer, wherein each of the at least two sensors includes an on-site electronics having a memory;
    calibrating the at least two sensors in parallel and independently of one another via a calibration routine by means of the data processing unit, wherein the data processing unit executes an operating program, including the calibration routine, associated with said data processing unit;
    instantiating the operating program multiple times, wherein each instance of the operating program is associated uniquely with one of the at least two sensors connected to the data processing unit;
    executing each instance of the operating program by the processor in parallel with and independently of other instances such that the at least two sensors are calibrated independently of one another; and
    storing calibration data ascertained during the calibrating in each corresponding memory of the at least two sensors by means of the operating program,
    wherein the measurement transmitter is structured to convert measurement signals from the at least two sensors into measured values using the calibration routine and to perform temperature compensation of the measured values, and is configured to access each memory for executing the operating program, and
    wherein the calibration routine, executable by the processor of the measurement transmitter, includes determining for each sensor when a stable measured value of each corresponding measured value is attained based on predetermined stability criteria, whereupon each stable measured value is stored temporarily, adapting calibration parameters of the sensors based on the stable measured value stored temporarily by the calibration routine, and storing the adapted calibration parameters in the corresponding memories of the sensors.

8. The method as claimed in claim 7, wherein:
    the at least two sensors are embodied for measuring one and the same parameter; and
    the at least two sensors are placed simultaneously in contact with a calibration medium and the measured values registered by the sensors are output to the data processing unit and used by the data processing unit for calibration.

9. The method as claimed in claim 7, further comprising:
bringing the at least two sensors in contact with a calibration medium;
registering calibration measured values of the at least two sensors; and
recording by means of the operating program and displaying by means of a display system of the data processing unit said calibration measured values.

10. The method as claimed in claim 7, wherein the at least two sensors are pH-sensors.

* * * * *